United States Patent [19]

Uno et al.

[11] 4,238,620
[45] Dec. 9, 1980

[54] DIBENZ[b,f]OXEPIN AND DIBENZO[b,f]THIEPIN DERIVATIVES, PROCESS FOR PREPARATION THEREOF, METHOD OF USING THE SAME, AND COMPOSITIONS THEREOF

[75] Inventors: Hitoshi Uno, Takatsuki; Yasutaka Nagai, Mukou; Hideo Nakamura, Tenri, all of Japan

[73] Assignee: Dainippon Pharmaceutical Co., Ltd., Osaka, Japan

[21] Appl. No.: 13,477

[22] Filed: Feb. 21, 1979

[30] Foreign Application Priority Data

Feb. 17, 1978 [JP] Japan ............................ 53-18004

[51] Int. Cl.$^3$ ................ C07D 313/14; C07D 337/14
[52] U.S. Cl. .................................. 549/13; 424/275; 424/278; 260/333
[58] Field of Search ........................ 549/13; 260/333

[56] References Cited

U.S. PATENT DOCUMENTS 4,104,280  8/1978  Ackrell ............................... 549/12

FOREIGN PATENT DOCUMENTS 2754561  6/1978  Fed. Rep. of Germany ............ 549/13

OTHER PUBLICATIONS

Ackrell et al., J. Med. Chem., vol. 21, pp. 1035–1044 (1978).

*Primary Examiner*—John D. Randolph

*Attorney, Agent, or Firm*—Wenderoth, Lind & Ponack

[57] ABSTRACT

Novel dibenz[b,f]oxepin and dibenzo[b,f]thiepin derivatives of the formula

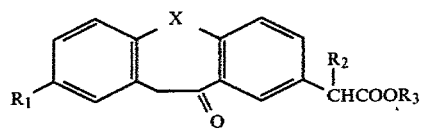

wherein X is an oxygen or sulfur atom, each of $R_1$ and $R_2$ is a hydrogen atom or a methyl group, and $R_3$ is a hydrogen atom or a 2-(2-hydroxyethoxy)ethyl group; provided that when $R_1$ is a hydrogen atom, the group

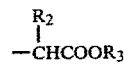

is a group other than a 1-carboxyethyl group; and when X is a sulfur atom, both $R_1$ and $R_2$ are methyl groups;

and pharmaceutically acceptable salts of said compounds in which $R_3$ is a hydrogen atom. Compositions of said compounds, processes for the preparation of said compounds, and a method of using said compounds are also provided. These novel compounds have excellent anti-inflammatory, analgesic and antipyretic activities.

10 Claims, 2 Drawing Figures

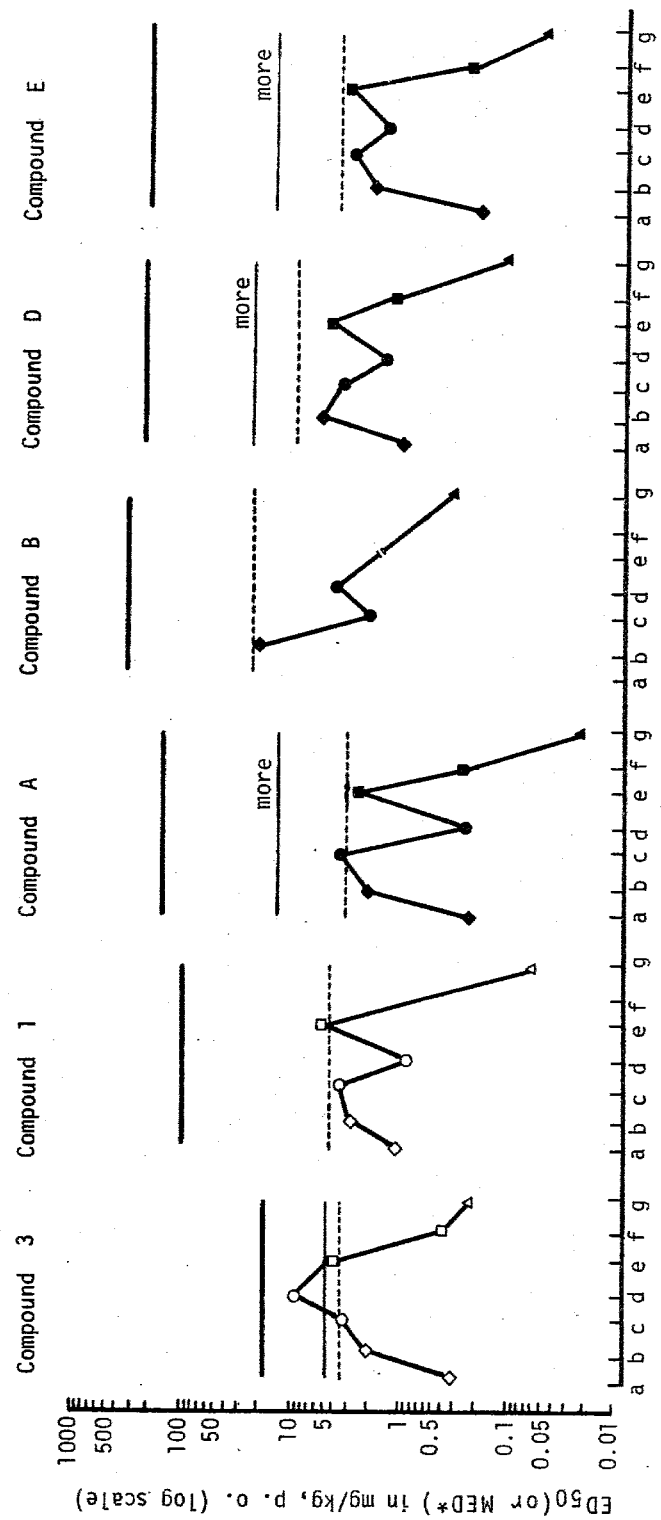

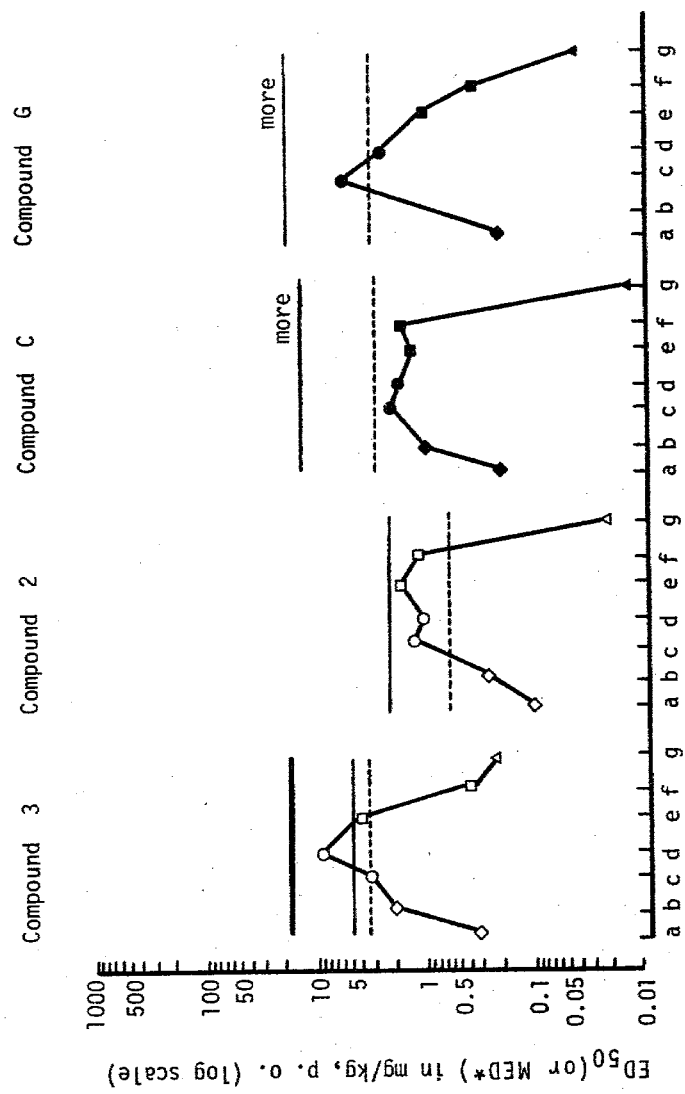

DIBENZ[b,f]OXEPIN AND DIBENZO[b,f]THIEPIN DERIVATIVES, PROCESS FOR PREPARATION THEREOF, METHOD OF USING THE SAME, AND COMPOSITIONS THEREOF

This invention relates to novel and useful 10,11-dihydro-11-oxodibenz[b,f]oxepin-2-acetic acid derivatives and 10,11-dihydro-11-oxodibenzo[b,f]thiepin-2-acetic acid derivatives.

British Pat. Nos. 1,476,214 and 1,476,215 disclose that dibenz[b,e]oxepin derivatives of the general formula

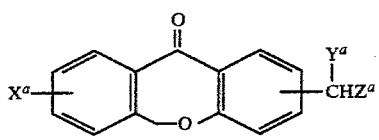

(II)

wherein $X^a$ represents a hydrogen or halogen atom or a trihalomethyl or lower alkoxy group, $Y^a$ represents a hydrogen atom or a lower alkyl group, and $Z^a$ represents a carboxyl, carbamyl or lower alkoxycarbonyl group,
have excellent analgesic, antipyretic and anti-inflammatory properties and a potent inhibitory action on platelet aggregation.

British Pat. No. 1,481,866 discloses compounds of formula (II) in which $X^a$ is an alkyl group having up to 4 carbon atoms in addition to the above compounds of formula (II), and states that these compounds are useful as anti-inflammatory agents and analgesic agents.

U.S. Pat. No. 4,000,308 discloses that dibenzo[b,e]-thiepin derivatives of the general formula

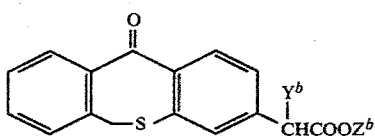

(III)

wherein $Y^b$ is hydrogen or a methyl group and $Z^b$ is hydrogen or an alkyl group containing 1 to 12 carbon atoms,
are useful as anti-inflammatory agents, platelet aggregation inhibitors, fibrinolytic agents and smooth muscle relaxants.

These British and U.S. Patents do not suggest at all the compounds of this invention which have quite a different skeleton.

DT-OS No. 2,754,561 (published on June 8, 1978, which is after the Convention priority date of the present application) states that propionic acid derivatives of the general formula

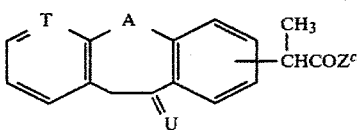

(IV)

wherein U represents an oxo group or two hydrogen atoms, T is CH or N, A is an oxygen or sulfur atom, and $Z^c$ is a hydroxyl group, an amino group, or an alkoxy group having 1 to 5 carbon atoms,
have outstanding anti-inflammatory activity, and specifically discloses 2-(10,11-dihydro-11-oxodibenz[b,f]oxepin-2-yl)propionic acid (to be referred to as compound 1), and 2-(10,11-dihydro-11-oxodibenzo[b,f]thiepin-2-yl)propionic acid (to be referred to as compound 2) which are similar to the compounds of the present invention.

J. Med. Chem., 21 (10), 1035–1044 (1978) discloses 10,11-dihydro-10-oxodibenzo[b,f]thiepin-2-acetic acid having an oxo group at the 10-position, and reports that its anti-inflammatory activity is 0.4 time that of phenylbutazone and its analgesic activity is equivalent to that of aspirin.

Some of the 10,11-dihydro-11-oxodibenz[b,f]oxepin-2-acetic acid derivatives of the present invention are far superior to compound 1 disclosed in the above-cited DT-OS in regard to pharmacological potency and/or safety margin.

The 10,11-dihydro-11-oxodibenzo[b,f]thiepin-2-acetic acid derivatives of this invention are far superior to compound 2 disclosed in the above-cited DT-OS in regard to safety margin.

The present invention pertains to dibenz[b,f]oxepin and dibenzo[b,f]thiepin derivatives of the general formula

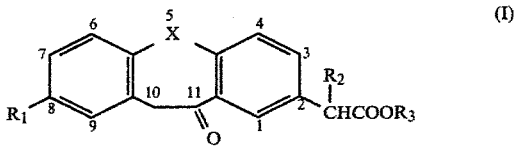

(I)

wherein X is an oxygen or sulfur atom, each of $R_1$ and $R_2$ is a hydrogen atom or a methyl group, and $R_3$ is a hydrogen atom or a 2-(2-hydroxyethoxy)ethyl group; provided that when $R_1$ is a hydrogen atom, the group

is a group other than a 1-carboxyethyl group; and when X is a sulfur atom, both $R_1$ and $R_2$ are methyl groups;
and pharmaceutically acceptable salts of said compounds in which $R_3$ is a hydrogen atom; processes for preparing these compounds; a method of using them; and to pharmaceutical compositions containing these compounds as active ingredients.

The compounds of formula (I) of this invention, therefore, include:

(1) when X is an oxygen atom,
   (i) both $R_1$ and $R_2$ are hydrogen atoms, and $R_3$ is a hydrogen atom or a 2-(2-hydroxyethoxy)ethyl group,
   (ii) $R_1$ is a hydrogen atom, $R_2$ is a methyl group, and $R_3$ is a 2-(2-hydroxyethoxy)ethyl group, and
   (iii) $R_1$ is a methyl group, $R_2$ is a hydrogen atom or a methyl group, and $R_3$ is a hydrogen atom or a 2-(2-hydroxyethoxy)ethyl group;

(2) when X is a sulfur atom,
   (iv) both $R_1$ and $R_2$ are methyl groups and $R_3$ is a hydrogen atom, and
   (v) both $R_1$ and $R_2$ are methyl groups, and $R_3$ is a 2-(2-hydroxyethoxy)ethyl group.

When $R_3$ is a hydrogen atom in groups (i), (iii) and (iv), these compounds of this invention include pharmaceutically acceptable salts of such compounds.

The pharmaceutically acceptable salts denote salts of these compounds with pharmaceutically acceptable inorganic or organic bases. The salts of inorganic bases include sodium, potassium, calcium, magnesium, aluminum and ammonium salts, and the salts of organic bases include salts with isopropylamine, diethylamine, ethanolamine, piperidine, tromethamine, and lysine.

Compounds of formula (I) in which $R_2$ is methyl contain an asymmetric carbon atom, and therefore, can exist in racemic form or as their optical antipodes. The present invention also embraces these racemic mixtures and optical antipodes.

The compounds of this invention have excellent anti-inflammatory, analgesic and antipyretic activities. Some of them exhibit activities comparable to, or greater than, indomethacin. Since these compounds have very weak toxicity and fairly weak side effect (ulcerogenicity in the gastrointestinal tract) for their high anti-inflammatory, analgesic and antipyretic activities, these compounds have a broader safety margin than indomethacin. The pharmacological activities of the compounds of this invention are characterized by the fact that their antipyretic activity is especially strong.

It is an object of the present invention to provide novel dibenz[b,f]oxepin and dibenzo[b,f]thiepin derivatives and their pharmaceutically acceptable salts having excellent anti-inflammatory, analgesic and antipyretic activities.

Another object of the invention is to provide processes for the preparation of the dibenz[b,f]oxepin and dibenzo[b,f]thiepin derivatives and their pharmaceutically acceptable salts.

A further object of the invention is to provide a method of treating inflammatory conditions which comprises administering an effective amount of the dibenz[b,f]oxepin or dibenzo[b,f]thiepin derivatives or their pharmaceutically acceptable salts.

A still further object of the invention is to provide a pharmaceutical composition comprising the dibenz[b,f]oxepin or dibenzo[b,f]thiepin derivatives or their pharmaceutically acceptable salts as an active ingredient.

These and other objects will be more apparent from the following description.

Compounds of formula (I) in which at least one of $R_1$ and $R_2$ represents a methyl group, i.e. compounds of groups (ii), (iii), (iv) and (v), are preferred in the present invention. Specific examples of these compounds are:

dl-2-(8-methyl-10,11-dihydro-11-oxodibenz[b,f]oxepin-2-yl)propionic acid (to be referred to as compound A), 8-methyl-10,11-dihydro-11-oxodibenz[b,f]oxepin-2-acetic acid (to be referred to as compound B), dl-2-(8-methyl-10,11-dihydro-11-oxodibenzo[b,f]2-yl)propionic acid (to be referred to as compound C), 2-(2-hydroxyethoxy)ethyl dl-2-(10,11-dihydro-11-oxodibenz[b,f]oxepin-2-yl)propionate (to be referred to as compound D), 2-(2-hydroxyethoxy)ethyl dl-2-(8-methyl-10,11-dihydro-11-oxodibenz[b,f]oxepin-2-yl)propionate (to be referred to as compound E), 2-(2-hydroxyethoxy)ethyl 8-methyl-10,11-dihydro-11-oxodibenz[b,f]oxepin-2-acetate (to be referred to as compound F), and 2-(2-hydroxyethoxy)ethyl dl-2-(8-methyl-10,11-dihydro-11-oxodibenzo[b,f]thiepin-2-yl)propionate (to be referred to as compound G).

Of these, compounds A, B, C, D, E and G, above all compounds A, C, D and E, are especially preferred.

Compounds of this invention having the following formula (Ia) corresponding to formula (I) in which $R_3$ is a hydrogen atom,

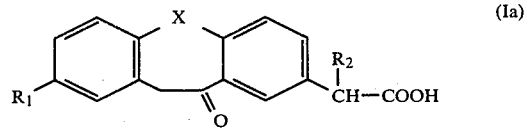

(Ia)

can be obtained, for example, by cyclizing phenylacetic acid derivatives of the general formula

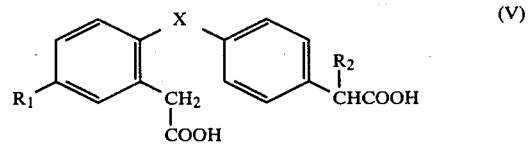

(V)

wherein $R_1$, $R_2$ and X are as defined hereinabove.

Cyclization of the compounds (V) to the compounds (Ia) can be performed in a manner known per se. For example, the compound (V) is directly cyclized in the presence of a condensing agent; or the compound (V) is first converted to a dicarboxylic acid halide by using a halogenating agent such as thionyl chloride, phosphorus pentachloride, or phosphorus tribromide and then the halide is cyclized by a Friedel-Crafts reaction, followed by hydrolyzing the cyclized product.

The condensing agent used in the direct cyclization process can be a condensing agent which is applicable to intramolecular acylation, for example polyphosphoric acid, a polyphosphate ester, phosphorus pentoxide or hydrogen fluoride. This reaction is carried out in the absence of solvent, or in an inert solvent such as benzene, toluene or xylene. The reaction temperature varies according to the type of the condensing agent, etc., but usually, it is from room temperature to about 150° C. When the condensing agent is polyphosphoric acid or a polyphosphate ester, it is convenient to use the condensing agent in excess to make it serve also as a solvent.

The cyclization of the dicarboxylic acid halide by a Friedel-Crafts reaction is effected in a customary manner. For example, an aprotic inert solvent such as nitrobenzene, dichloromethane or carbon disulfide, and a known Lewis acid catalyst such as aluminum chloride or zinc chloride can be used. The subsequent hydrolysis of the product is performed by a known method, for example, by contacting the product with an aqueous solution of a base such as sodium hydroxide, potassium hydroxide, sodium carbonate or potassium carbonate.

Compounds of the following formula (Ib) which corresponds to formula (I) in which $R_3$ is a 2-(2-hydroxyethoxy)ethyl group,

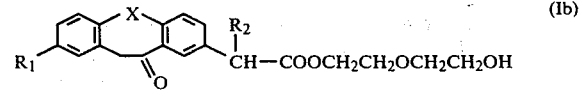

(Ib)

can be obtained by esterifying in a customary manner the carboxylic acids of formula (I')

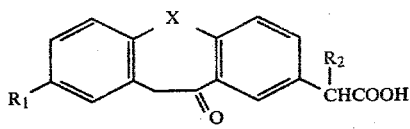
(I')

wherein X is an oxygen or sulfur atom, and $R_1$ and $R_2$ each are a hydrogen atom or a methyl group; provided that when X is a sulfur atom, both $R_1$ and $R_2$ are methyl groups, obtained by the above method or the reactive derivatives thereof. For example, the esters can be obtained by reacting the carboxylic acid (I') or its reactive derivative with a compound of the general formula

wherein Q is a hydroxyl group or an ester-forming functional group, and Y is a hydroxyl group or a protected hydroxyl group convertible to a hydroxyl group, and if desired, splitting off the protective group of the protected hydroxyl group.

Examples of the reactive derivatives of carboxylic acids include metal salts, especially alkali metal salts such as sodium or potassium salts, carboxylic acid halides, mixed acid anhydrides, and lower alkyl or aryl esters. The ester-forming functional group includes, for example, halogen atoms having an atomic number of 17 or more, i.e. chlorine, bromine and iodine, and organic sulfonyloxy groups, for example arylsulfonyloxy groups such as benzenesulfonyloxy or p-toluenesulfonyloxy, and alkylsulfonyloxy groups such as methanesulfonyloxy group. Protective groups for hydroxyl may include groups capable of being split off by hydrogenolysis, such as benzyl, trityl and benzyloxycarbonyl groups and groups capable of being split off by hydrolysis, such as a trityl group.

The metal salts of the carboxylic acids (I') react with compounds of formula (VI) in which Q is an ester-forming functional group such as a halogen atom or an organic sulfonyloxy group, and the carboxylic acids (I') or the other reactive derivatives react with compounds of formula (VI) in which Q is a hydroxyl group. These reactions can be performed under ordinary esterification conditions.

For example, the reaction of the metal salts of the carboxylic acids (I') with the compounds of formula (VI) in which Q is an ester-forming functional group such as a halogen atom or an organic sulfonyloxy group is usually carried out in a solvent. Specific examples of the solvent are aprotic inert solvents such as dimethylformamide, benzene, toluene and xylene. The reaction temperature is usually about 50° C. to about 150° C.

The reaction of the carboxylic acids (I') with the compounds of formula (VI) in which Q is a hydroxyl group is carried out in the absence of a solvent or in a solvent in the presence of, for example, a strong acid. The solvent includes, for example, an aprotic inert solvent such as benzene, toluene, xylene, dichloroethane, tetrahydrofuran, and dioxane. When the compound of formula (VI) is diethylene glycol, it may be used in excess to make it serve also as a reaction solvent. Examples of the strong acid are sulfuric acid, hydrogen chloride, boron trifluoride, and p-toluenesulfonic acid.

When the compound of formula (VI) is diethylene glycol, it is preferred to use the diethylene glycol in a stoichiometrically excessive amount in order to avoid the formation of a bis-compound. Usually, the diethylene glycol is used in an amount of at least 1.5 moles per mole of the carboxylic acid (I'). Usually, the reaction temperature is about 50° C. to about 150° C.

The halides and mixed anhydrides of the carboxylic acids (I') can be prepared in a customary manner. The reaction of these derivatives with the compounds of formula (VI) in which Q is a hydroxyl group is carried out under ordinary reaction conditions.

The lower alkyl or aryl esters of the carboxylic acids (I') are obtained by reacting the carboxylic acids (I') with lower alkanols in the presence of strong acids, or reacting them with diaryl carbonates. The reaction of these esters with the compounds of formula (VI) in which Q is a hydroxyl group is carried out under ordinary transesterification conditions.

When the product is obtained in the form in which the hydroxyl group is protected, the protective group is split off by, for example, hydrogenolysis or hydrolysis of the compound thereby to form a compound of formula (I) in which $R_3$ is a 2-(2-hydroxyethoxy)ethyl group. The hydrogenolysis can be performed in a customary manner. For example, it is carried out in a solvent such as methanol, ethanol or isopropanol in the presence of a noble metal catalyst such as palladium-on-carbon at room temperature. The hydrolysis is carried out under mild conditions, for example, at room temperature in a mixture of water and acetic acid.

The compounds (I) of this invention produced by the aforesaid reactions are isolated and purified in a customary manner.

Racemic mixtures of compounds of formula (I) in which $R_2$ is methyl and $R_3$ is hydrogen are optically resolved in a customary manner by using optically active bases such as cinchonidine and d- or l-α-methylbenzylamine which are used generally as resolving agents, thereby to form the individual optical antipodes.

Compounds of formula (I) in which $R_3$ is hydrogen can be converted to salts by treatment with inorganic or organic bases in a customary manner. Specific examples of the inorganic and organic bases are sodium hydroxide, potassium hydroxide, calcium hydroxide, magnesium hydroxide, aluminum hydroxide, ammonium hydroxide, isopropylamine, diethylamine, ethanolamine, piperidine, tromethamine, and lysine. This reaction is carried out at about 0° C. to about 100° C. in a lower alkanol (e.g., methanol, ethanol or isopropanol), toluene or a mixture thereof. The calcium salts and magnesium salts can be obtained by treating the corresponding sodium salts or potassium salts with calcium chloride or magnesium chloride, respectively.

The starting compounds (V) are novel compounds, and can be prepared, for example, by the following procedure.

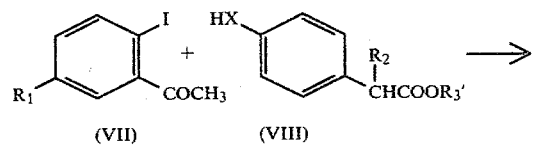

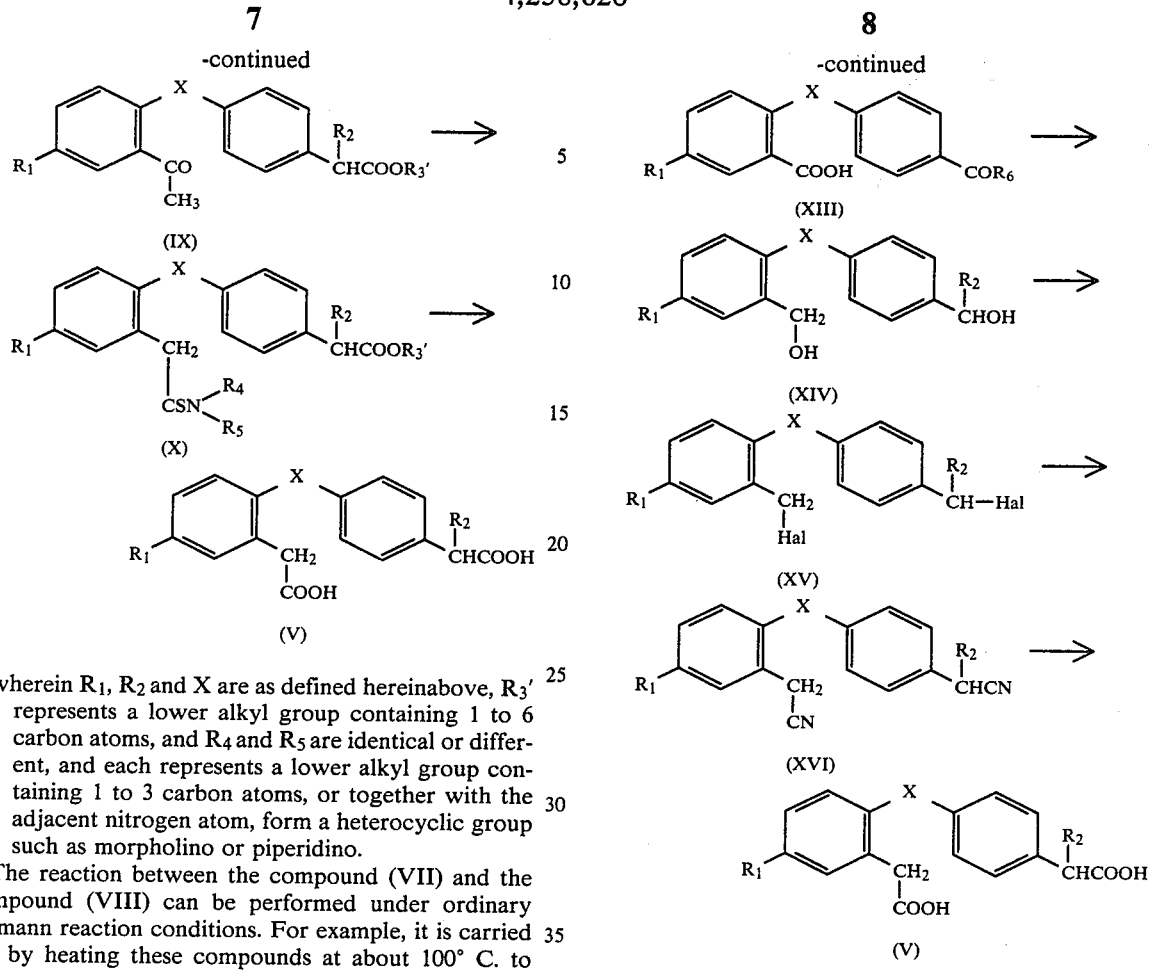

wherein $R_1$, $R_2$ and X are as defined hereinabove, $R_3'$ represents a lower alkyl group containing 1 to 6 carbon atoms, and $R_4$ and $R_5$ are identical or different, and each represents a lower alkyl group containing 1 to 3 carbon atoms, or together with the adjacent nitrogen atom, form a heterocyclic group such as morpholino or piperidino.

The reaction between the compound (VII) and the compound (VIII) can be performed under ordinary Ullmann reaction conditions. For example, it is carried out by heating these compounds at about 100° C. to about 200° C. in a solvent such as nitrobenzene or dimethylformamide in the presence of a catalyst such as copper powder and a base such as potassium carbonate, sodium carbonate, potassium hydroxide, sodium hydroxide or sodium methylate.

Conversion to the compound (X) can be performed under ordinary Willgerodt-Kindler reaction conditions. For example, a mixture consisting of 1 mole of the compound (IX), 1 to 1.5 moles of sulfur and 1 to 2 moles of a secondary amine is heated at about 100° C. to about 200° C. in the absence of solvent or in a solvent such as dioxane to form the compound (X). Specific examples of the secondary amines are dimethylamine, morpholine and piperidine. Morpholine is especially preferred.

The hydrolysis of the compound (X) to the compound (V) can be performed in a customary manner. For example, it is carried out by heating the compound (X) at about 100° C. to about 150° C. in a mixture of acetic acid and sulfuric acid, or by heating the compound (X) in a mixture of water and a lower alkanol (e.g., ethanol or isopropanol) in the presence of a base such as sodium hydroxide or potassium hydroxide.

The compound (V) can also be produced by the following procedure.

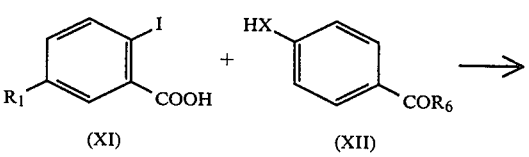

In the formulae, $R_1$, $R_2$ and X are as defined hereinabove, $R_6$ represents a methyl group or a lower alkoxy group containing 1 to 6 carbon atoms, and Hal represents a halogen atom having an atomic number of 17 or more.

The reaction between the compound (XI) and the compound (XII), like the reaction between the compound (VII) and the compound (VIII), can be performed under ordinary Ullmann reaction conditions.

Reduction of the compound (XIII) to the compound (XIV) can be performed in a customary manner. For example, it is carried out by reacting the compound (XIII) with a metal hydride complex such as lithium aluminum hydride at room temperature to about 70° C. in a solvent such as tetrahydrofuran or diethyl ether.

Halogenation of the compound (XIV) to the compound (XV) can be performed in a customary manner. For example, it is carried out by reacting the compound (XIV) with a halogenating agent such as thionyl chloride or phosphorus tribromide at room temperature to about 80° C. in the absence of solvent or in a solvent such as chloroform or benzene.

Cyanation of the compound (XV) to the compound (XVI) can be performed in a customary manner. For example, it is carried out by reacting the compound (XV) with a metal cyanide such as sodium cyanide or potassium cyanide in a solvent such as dimethyl sulfoxide or a mixture of water, ethanol, and dioxane.

Hydrolysis of the compound (XVI) to the compound (V) can be performed in a customary manner. For example, it is carried out by heating the compound (XVI)

in a solvent such as dilute ethanol in the presence of a base such as sodium hydroxide or potassium hydroxide.

The pharmacological activities of the compounds of this invention are described below with reference to the results of pharmacological tests conducted on the typical compounds of this invention, a commercially available anti-inflammatory agent and the compounds disclosed in DT-OS No. 2,754,561. The compounds tested are compounds A, B, C, D, E, F and G of the present invention, and as controls, compounds 1 and 2 of the above-cited DT-OS, and indomethacin (to be referred to as compound 3) which is a well-known anti-inflammatory agent having potent efficacy.

Ten to 15 animals for each dose of test compounds were used for testing anti-inflammatory, analgesic and antipyretic activities, and 4 to 6 dose levels were used for calculating each $ED_{50}$ (50% effective dose). Six to 15 animals for each dose and 4 to 6 dose levels were used for calculating each $UD_{50}$ (50% ulcer forming dose) or $LD_{50}$ (50% lethal dose).

TEST 1. ANTI-INFLAMMATORY ACTIVITY (1) Effect on acute inflammation:

(a) Carrageenin-induced hind paw oedema in rats (CAR method)

The test was carried out according to the method described in Proc. Soc. Exp. Biol. Med., 111, 544 (1962).

(b) Ultraviolet-induced erythema in guinea-pigs (UVE method)

The test was carried out according to the method described in Arch. Int. Pharmacodyn. Ther., 116, 261 (1958).

(2) Effect on subacute and chronic inflammations:

(a) Therapeutic activity on adjuvant-induced arthritis in rats (AAT method)

The test was carried out according to the method described in Brit. J. Pharmacol., 21, 127 (1963) and Japan J. Pharmacol., 23, 58 (1973).

(b) Felt pellet-induced granuloma formation in rats (FGF method)

The test was carried out according to the method described in J. Amer. Pharm. Assoc., 46, 515 (1957) and Chem. Pharm. Bull., 23, 1446 (1975).

TEST 2. ANALGESIC ACTIVITY (a) $AgNO_3$-induced joint pain in rats (AGP method)

The test was carried out according to the method described in J. Pharmacol. Expt. Ther., 98, 19 (1950)

(b) Acetic acid (AcOH)-induced writhing in rats (ACW method)

The test was carried out according to the method described in Arzneim. Forsch., 25, 1505 (1975).

TEST 3. ANTIPYRETIC ACTIVITY

Yeast-induced fever in rats (YEF method)

The test was carried out according to the method described in Arzneim. Forsch., 13, 338 (1963).

TEST 4. ULCEROGENICITY IN GASTROINTESTINAL TRACT

Gastrointestinal ulcer formation in fed rats

The test was carried out according to the method described in Science, 170, 183 (1970).

TEST 5. LETHAL TOXICITY (a) Single administration in rats

The mortality was observed on the 7th day after single administration of test compounds, and $LD_{50}$-value was calculated according to the method of Litchfield and Wilcoxon.

(b) Repeated administrations in rats

Test compounds were orally administered once daily for 5 days, and $LD_{50}$-value was calculated from the mortality on the 6th day.

Tables I to III summarize the results of Tests 1 to 5. $ED_{50}$ (anti-inflammatory, analgesic and antipyretic activities), $UD_{50}$ and $LD_{50}$ values of these compounds are shown in FIGS. 1 and 2. From these diagrams, the correlation between the pharmacological activity of each compound and its ulcerogenicity and toxicity, i.e. the safety margin of each compound, can be clearly seen. In these Figures, the lines and letters have the following meanings:

| | |
|---|---|
| a: Anti-inflammatory activity | (AAT method) |
| b: Anti-inflammatory activity | (FGF method) |
| c: Anti-inflammatory activity | (CAR method) |
| d: Anti-inflammatory activity | (UVE method) |
| e: Analgesic activity | (AGP method) |
| f: Analgesic activity | (ACW method) |
| g: Antipyretic activity | (YEF method) |
| $LD_{50}$ (single administration) | |
| —— $LD_{50}$ (repeated administration) | |
| $UD_{50}$ | |

$$R_1 \underset{\underset{O}{\|}}{\overset{X}{\bigcirc\bigcirc}} \overset{R_2}{\underset{CHCOOR_3}{|}}$$

TABLE I

| | | | | Anti-inflammatory activity | | | |
|---|---|---|---|---|---|---|---|
| | | | | $ED_{50}$ (mg/kg, p.o.) | | | |
| | | | | | | Subacute and chronic | |
| Test compound | | | | Acute inflammation | | inflammation | |
| | X | $R_1$ | $R_2$ | $R_3$ | CAR | UVE | AAT* | FGF* |
| A | O | Me | Me | H | 3.38 | 0.30 | 0.2 | 2.0 |
| B | O | Me | H | H | 2.20 | 4.48 | — | 20.0 |
| C | S | Me | Me | H | 2.08 | 0.85 | <0.2 | 1.0 |
| D | O | H | Me | 2-HEE | 2.87 | 1.50 | 1.0 | 6.0 |
| E | O | Me | Me | 2-HEE | 3.61 | 1.41 | 0.2 | 2.0 |
| F | O | Me | H | 2-HEE | 7.95 | — | — | — |
| G | S | Me | Me | 2-HEE | 5.94 | 2.52 | ≦0.2 | — |
| 1 | O | H | Me | H | 3.65 | 0.93 | 1.0 | 3.0 |
| 2 | S | H | Me | H | 1.20 | 0.98 | <0.1 | 0.25 |
| 3 | (Indomethacin) | | | | 3.30 | 9.12 | 0.2–0.4 | 2.0 |

2-HEE: —$(CH_2)_2O(CH_2)_2OH$
*Minimum Effective Dose in mg/kg/day, p.o.

TABLE II

| | Analgesic and antipyretic activities | | |
|---|---|---|---|
| | $ED_{50}$ (mg/kg, p.o.) | | |
| | Analgesic | | Antipyretic |
| Test compound | AGP | ACW | YEF |
| A | 2.60 | 0.28 | 0.021 |
| B | — | — | 0.357 |
| C | 1.41 | 0.84 | 0.015 |
| D | 4.60 | 1.06 | 0.112 |
| E | 3.80 | 0.27 | 0.055 |
| G | 0.96 | 0.33 | 0.041 |
| 1 | 5.80 | — | 0.062 |
| 2 | 1.66 | 1.16 | 0.022 |

TABLE II-continued

| | Analgesic and antipyretic activities | | |
|---|---|---|---|
| | | $ED_{50}$ (mg/kg, p.o.) | |
| | Analgesic | | Antipyretic |
| Test compound | AGP | ACW | YEF |
| 3 | 4.10 | 0.44 | 0.223 |

TABLE III

| | Ulcerogenicity and lethal toxicity | | |
|---|---|---|---|
| Test Compound | $UD_{50}$ (mg/kg, p.o.) | $LD_{50}$ (mg/kg, p.o.) | |
| | | Single | Repeated |
| A | 2.97 | 147 | >12 |
| B | 22.1 | 326 | >60 |
| C | 2.76 | — | >12 |
| D | 10.9 | 260 | >24 |
| E | 4.04 | 219 | >16 |
| F | 36.8 | — | — |
| G | 2.94 | — | >16 |
| 1 | 4.85 | 106 | — |
| 2 | 0.62 | — | 2.15 |
| 3 | 3.95 | 18.5 | ca. 5.0 |

The following conclusions can be drawn from Tables I to III and FIGS. 1 and 2. In the following description, the therapeutic index means $LD_{50}/ED_{50}$ (or MED), and the safety index means $UD_{50}/ED_{50}$ (or MED). The safety margin of a given compound is broader when it has larger therapeutic and or safety indices.

(i) The anti-inflammatory, analgesic and antipyretic activities of compounds A, C, E and G are equivalent or superior to those of indomethacin (compound 3). The anti-inflammatory (acute), analgesic and antipyretic activities of compound D are almost equivalent to those of indomethacin, though its activity on subacute and chronic inflammation is inferior to that of indomethacin.

(ii) The toxicities of compounds A, B, C, D, E and G are far weaker than those of indomethacin, and therefore, these compounds have far larger therapeutic indices than indomethacin.

(iii) It is seen from FIGS. 1 and 2 that in compounds A, B, C, D, E and G, anti-inflammatory, analgesic and antipyretic activities are more separated from ulcerogenicity in the gastrointestinal tract than in indomethacin. Especially good separation is noted in compounds B, C, D and E.

(iv) Compound A corresponding to a compound resulting from the introduction of a methyl group into the 8-position of compound 1 has stronger pharmacological activities in all the methods tested when compound 1. In particular, compound A is about 2 to 5 times as potent as compound 1 when tested by the UVE, AAT, AGP and YEF methods. In addition, the average therapeutic index of compound A is about 3.7 times that of compound 1 since compound A is less toxic than compound 1. Furthermore, the average safety index of compound A is about 1.6 times that of compound 1.

As is clearly understood from the above explanation, compound A is superior to compound 1 not only in pharmacological activities but also in safety margin.

(v) On the whole, the pharmacological activities of compound D, which is a 2-(2-hydroxyethoxy)ethyl ester of compound 1, are comparable to those of compound 1, though some of the pharmacological activities of compound D are slightly inferior to those of compound 1. On the other hand, both the ulcerogenicity and toxicity of compound D are less than one-half of those of compound 1. Hence, the safety and therapeutic indices of compound D are about two times as great as those of compound 1, and thus, compound D is far superior to compound 1 in the breadth of the safety margin.

(vi) The activity of compound B on acute inflammation and fever is nearly comparable to that of indomethacin. In addition, compound B has very weak ulcerogenicity and toxicity. Its ulcerogenicity and toxicity are about 1/6 and about 1/18, respectively, of those of indomethacin.

(vii) The pharmacological activities of compound E, which is a 2-(2-hydroxyethoxy)ethyl ester of compound A, are somewhat inferior to those of compound A, but are equivalent to, or more potent, than those of compound 1, The ulcerogenicity and toxicity and compound E are weaker than those of compound A, and its average safety and therapeutic indices are comparable to those of compound A. Accordingly, compound E is better and somewhat better than compound 1 in regard to the breadth of safety margin and pharmacological activities, respectively.

(viii) The pharmacological activities of compound C, which is a compound resulting from the introduction of a methyl group into the 8-position of compound 2, are comparable or slightly inferior to those of compound 2. On the other hand, the ulcerogenicity and toxicity of compoynd C are about 1/4 and less than 1/6, respectively, of those of compound 2. Accordingly, the average safety and therapeutic indices of compound C are about 4 times and more than 5 times those of compound 2, and compound C is far superior to compound 2 in regard to the breadth of the safety margin.

(ix) The analgesic activity of compound G, which is a 2-(2-hydroxyethoxy)ethyl ester of compound C, is stronger than those of compounds 2 and C, though its antiinflammatory and antipyretic activities are weaker than those of compounds 2 and C. On the other hand, the ulcerogenicity and toxicity of compound G are about 1/5 and less than 1/7, respectively, of those of compound 2. Accordingly, the average safety and therapeutic indices of compound G are about 5 times and more than 8 times those of compound 2, respectively, and compound G is far superior to compound 2 in regard to the breadth of the safety margin.

As is clearly seen from the experimental results given hereinabove, the compounds of this invention exhibit superior anti-inflammatory, analgesic and antipyretic activities which are well separated from ulcerogenicity in the gastrointestinal tract. Moreover, these compounds have low toxicity. Hence, the compounds of formula (I) of this invention and pharmaceutically acceptable salts thereof can be used for the treatment of various inflammatory conditions of the muscular skeletal system, skeletal joints and other tissues, for example, inflammatory conditions such as rheumatism, concussion, laceration, arthritis, bone fractures, post-traumatic conditions, and peritendinitis, as analgesic and anti-inflammatory agents. When these conditions include pain and fever coupled with inflammation, the compounds of this invention are useful for the relief of these conditions as well as inflammation.

The administration routes of these compounds may be oral, parenteral, intrarectal or topical. In topical administration, compounds of formula (I) in which $R_3$ is a 2-(2-hydroxyethoxy)ethyl group are especially preferred. The dosage of the compounds of formula (I) of this invention or the pharmaceutically acceptable salts thereof vary according to the kinds of the compounds, the method of administration, the condition of the patient, and the age of the patient, etc. Usually, it is 0.2 to 20 mg per kg of body weight of the patient per day, preferably 0.3 to 10 mg per kg of body weight of the patient per day, for human-being adult as well as child. The drug can be administered once to several times a day.

The compounds of formula (I) and the pharmaceutically acceptable salts thereof are usually applied in the form of pharmaceutical compositions prepared by mixing them with pharmaceutically acceptable carriers. Such carriers are those which are normally used in pharmaceutical preparation and do not react with the compounds of formula (I) and the salts thereof. Specific examples include lactose, starch, sucrose, microcrystalline cellulose, sodium carboxymethylcellulose, calcium carboxymethylcellulose, methylcellulose, gelatin, acacia, hydroxypropylcellulose, polyvinylpyrrolidone, light anhydrous silicic acid, magnesium stearate, talc, tragacanth, bentonite, veegum, carboxyvinyl polymer, sorbitan fatty acid esters, sodium lauryl sulfate, cacao butter, glycerides of saturated fatty acids, ahydrous lanolin, glycerogelatin, macrogol, vegetable oils, wax, cetyl alcohol, oleyl alcohol, propylene glycol, ethanol, isopropanol, benzyl alcohol, and water. The pharmaceutical compositions can be in any desired dosage form such as tablets, capsules, granules, fine granules, powders, syrups, suppositories, ointments, creams, gels, and injections. These preparations can be formed in a customary manner. Liquid preparations may be those which are to be dissolved or suspended in water or suitable media before use. The tablets may be coated in a known manner.

Usually, these compositions contain at least 0.1%, preferably 0.5% to 70%, of the compounds of formula (I) or the pharmaceutically acceptable salts thereof as active ingredients. Furthermore, these compositions may further contain other therapeutically effective compounds.

The present invention is illustrated more specifically by the following Examples and Reference Examples. It should be understood that the invention is not limited to these examples. The compounds were identified by elemental analysis, mass spectroscopy, IR spectroscopy, NMR spectroscopy, etc.

EXAMPLE 1 dl-2-(8-Methyl-10,11-dihydro-11-oxodibenz[b,f]oxepin-2-yl)propionic acid (compound A):

A mixture of dl-2-[4-(2'-carboxymethyl-4'-methylphenoxy)phenyl]propionic acid (15.3 g) and polyphosphoric acid (92 g) was heated with stirring at 110°–120° C. for 2 hours. To the reaction mixture was added water and the resulting mixture was extracted with chloroform. The organic layer was washed with water, dried over anhydrous sodium sulfate and concentrated. The residue was chromatographed on silica gel (75 g) using chloroform as an eluent to give a crude product, which was recrystallized from toluene to give the title compound (9.4 g, 65.3%), m.p. 128°–129° C.

EXAMPLE 2

8-Methyl-10,11-dihydro-11-oxodibenz[b,f]oxepin-2-acetic acid (compound B):

A mixture of 4-(2'-carboxymethyl-4'-methylphenoxy)phenylacetic acid (8.5 g) and polyphosphoric acid (51 g) was stirred at 130° C. for 30 minutes. After cooling, the resulting mixture was poured into ice-water and the resulting mixture was extracted with ethyl acetate. The extracts were washed with water, dried over anhydrous sodium sulfate and concentrated in vacuo. The residue was recrystallized from toluene to give the title compound (6.7 g, 84%), m.p. 154°–155° C.

EXAMPLE 3

10,11-Dihydro-11-oxodibenz[b,f]oxepin-2-acetic acid:

Repeating the procedure of Example 2 using 4-(2'-carboxymethylphenoxy)phenylacetic acid in place of 4-(2'-carboxymethyl-4'-methylphenoxy)phenylacetic acid gave the title compound, m.p. 158°–160° C.

EXAMPLE 4 dl-2-(8-Methyl-10,11-dihydro-11-oxodibenzo[b,f]thiepin-2-yl)propionic acid (compound C):

A mixture of dl-2-[4-(2'-carboxymethyl-4'-methylphenylthio)phenyl]propionic acid (3.4 g) and polyphosphoric acid (27 g) was stirred at 120°–130° C. for 2 hours. The reaction mixture was poured into ice-water and the resulting mixture was extracted with chloroform. The extracts were dried over anhydrous sodium sulfate and concentrated. The oily residue was chromatographed on silica gel (25 g) using chloroform as an eluent to give a solid product, which was recrystallized from toluene to give the title compound (2.1 g, 64%), m.p. 157°–159° C.

EXAMPLE 5

2-(2-Hydroxyethoxy)ethyl dl-2-(10,11-dihydro-11-oxodibenz[b,f]oxepin-2-yl)propionate (compound D):

To dl-2-(10,11-dihydro-11-oxodibenz[b,f]oxepin-2-yl)propionic acid (1.5 g) was added a mixture of concentrated sulfuric acid (0.3 ml) and diethylene glycol (5 ml) and the resulting solution was stirred at 100° C. for 2 hours. To the mixture was added chloroform and the solution was washed with aqueous sodium carbonate and water. The chloroform layer was dried over anhydrous sodium sulfate and concentrated. The residue was chromatographed on silica gel (20 g) using chloroform as an eluent. Fractions containing the title compound were pooled and concentrated on a water bath. The residue was heated at 100° C. for 3 hours reduced pressure (5 mmHg) to remove the remaining solvent. The title compound was obtained as an oil (1.87 g, 95%).

Analysis—Calcd. for $C_{21}H_{22}O_6$: C, 68.09, H, 5.88; Found: C, 67.79; H, 5.80

Mass Spectrum m/e: 370 (M+) IR$\nu_{max}^{film}$cm$^{-1}$: 1725 (C=O)

EXAMPLE 6

2-(2-Hydroxyethoxy)ethyl 8-methyl-10,11-dihydro-11-oxodibenz[b,f]oxepin-2-acetate (compound F):

Repeating the procedure of Example 5 using 8-methyl-10,11-dihydro-11-oxodibenz[b,f]oxepin-2-acetic acid in place of dl-2-(10,11-dihydro-11-oxodibenz[b,f]oxepin-2-yl)propionic acid gave the title compound as an oil.

Analysis—Calcd. for $C_{21}H_{22}O_6$: C, 68.09; H, 5.88; Found: C, 67.85; H, 5.72

Mass Spectrum m/e: 370 (M+)
IR$\nu_{max}^{film}$cm$^{-1}$: 1725 (C=O)

EXAMPLE 7

2-(2-Hydroxyethoxy)ethyl 10,11-dihydro-11-oxo-dibenz[b,f]oxepin-2-acetate:

Repeating the procedure of Example 5 using 10,11-dihydro-11-oxodibenz[b,f]oxepin-2-acetic acid in place of dl-2-(b 10,11-dihydro-11-oxodibenz[b,f]oxepin-2-yl)propionic acid gave the title compound as an oil.

Analysis—Calcd. for $C_{20}H_{20}O_6$: C, 67.40; H, 5.66; Found: C, 67.17; H, 5.53

Mass Spectrum m/e: 356 (M+)

$IR\nu_{max}^{film}cm^{-1}$: 1725 (C=O)

EXAMPLE 8

2-(2-Hydroxyethoxy)ethyl dl-2-(8-methyl-10,11-dihydro-11-oxodibenz[b,f]oxepin-2-yl)propionate (compound E):

A mixture of dl-2-(8-methyl-10,11-dihydro-11-oxodibenz[b,f]oxepin-2-yl)propionic acid (2.0 g) and potassium hydroxide (0.42 g) in methanol (40 ml) was heated on a water bath for 10 minutes. The reaction mixture was concentrated in vacuo and to the residue was added ethylene glycol β-chloroethyl ether (0.92 g) and toluene (40 ml). The resulting mixture was refluxed with stirring for 6 hours and then concentrated in vacuo. The residue was chromatographed on silica gel (18 g) using toluene and dichloromethane as eluents. The fractions eluted with dichloromethane were concentrated on a water bath. The residue was heated at 100° C. for 2 hours under reduced pressure (4 mmHg) to give the title compound as an oil (1.82 g, 70%).

Analysis—Calcd. for $C_{22}H_{24}O_6$: C, 68.73; H, 6.29; Found: C, 68.65; H, 6.32

Mass Spectrum m/e: 384 (M+)

$IR\nu_{max}^{film}cm^{-1}$: 1725 (C=O)

EXAMPLE 9

2-(2-Hydroxyethoxy)ethyl dl-2-(8-methyl-10,11-dihydro-11-oxodibenzo[b,f]thiepin-2-yl)propionate (compound G):

To dl-2-(8-methyl-10,11-dihydro-11-oxodibenzo[b,f]thiepin-2-yl)propionic acid (2.0 g) was added a mixture of concentrated sulfuric acid (0.4 ml) and diethylene glycol (7.0 g) and the resulting solution was stirred at 100°–110° C. for 2.5 hours. To the reaction mixture was added chloroform and the solution was washed with aqueous sodium carbonate and water. The chloroform layer was dried over anhydrous sodium sulfate and concentrated. The residue was chromatographed on silica gel (28 g) using chloroform as an eluent. Fractions containing the title compound were pooled and concentrated on a water bath. The residue was heated at 90° C. for 3 hours under reduced pressure (2 mmHg) to give the title compound (1.9 g, 72%) as an oil.

Analysis—Calcd. for $C_{22}H_{24}O_5S$: C, 65.98, H, 6.04, S, 8.01; Found: C, 65.71; H, 5.87, S, 8.21

Mass spectrum m/e: 400 (M+)

$IR\nu_{max}^{film}cm^{-1}$: 1725 (C=O)

EXAMPLE 10

Potassium dl-2-(8-methyl-10,11-dihydro-11-oxodibenz[b,f]oxepin-2-yl)propionate:

To a solution of dl-2-(8-methyl-10,11-dihydro-11-oxodibenz[b,f]oxepin-2-yl)propionic acid (1.0 g) in toluene (15 ml) was added a solution of potassium hydroxide (0.19 g) in methanol (10 ml). The resulting solution was heated on a water bath for 20 minutes and concentrated in vacuo to give the title compound (1.13 g) as a hygroscopic powder.

REFERENCE EXAMPLE 1 dl-2-[4-(2'-Carboxymethyl-4'-methylphenylthio)phenyl]propionic acid:

A mixture of p-mercaptohydratropic acid (9.7 g), 2-iodo-5-methylacetophenone (12.9 g), potassium carbonate (6.83 g) and copper (1.0 g) in pyridine (15 ml) was heated with stirring at 140°–150° C. for 3 hours and allowed to cool. Chloroform was added to the mixture. The resulting solution was washed with dilute hydrochloric acid and water, and dried over anhydrous sodium sulfate. The solution was concentrated to give crude methyl dl-2-[4-(2'-acetyl-4'-methylphenylthio)phenyl]propionate (16.1 g) as an oil.

Sulfur (2.2 g) and morpholine (8.5 ) were added to the resulting ester and the mixture was stirred at 140°–150° C. for 5 hours. Chloroform was added to the reaction mixture. The solution was washed with dilute hydrochloric acid and water, and concentrated to give crude methyl dl-2-[4-(4'-methyl-2'-morpholinothiocarbonylmethylphenylthio)phenyl]propionate (21 g).

The above thiomorpholide compound was dissolved in a mixture of acetic acid (93 ml), concentrated sulfuric acid (16.6 ml) and water (31 ml) and the solution was heated under reflux for 6 hours. The reaction mixture was poured into water and the resulting mixture was extracted with chloroform. The chloroform layer was washed with water and then extracted with aqueous sodium bicarbonate. The extracts were made acidic with dilute hydrochloric acid and extracted with chloroform. Concentration of the dried extracts gave an oil, which was dissolved in toluene (20 ml) with warming. The solution was cooled in an ice bath. The crystalline precipitate was collected and recrystallized from toluene to give the title compound (5.2 g, 32%), m.p. 144°–145° C.

The following compounds were prepared in substantially the same manner as in Referential Example 1:

4-(2'-Carboxymethylphenoxy)phenylacetic acid, m.p. 150°–152° C.

dl-2-[4-(2'-Carboxymethylphenoxy)phenyl]propionic acid, m.p. 170°–172° C.

4-(2'-Carboxymethyl-4'-methylphenoxy)phenylacetic acid, m.p. 159°–160° C.

dl-2-[4-(2'-Carboxymethyl-4'-methylphenoxy)phenyl]propionic acid, m.p. 129°–132° C.

REFERENCE EXAMPLE 2

2-(4'-Ethoxycarbonylphenoxy)benzoic acid:

Potassium carbonate (14 g) was added to a solution of 2-indobenzoic acid (50 g) in nitrobenzene (50 ml) at 140°–150° C. with stirring. The mixture was stirred for an additional 10 minutes after the addition. Then, ethyl 4-hydroxybenzoate (33.5 g), potassium carbonate (28 g) and copper (3 g) were added. The mixture was stirred at 150°–160° C. for 30 minutes and allowed to cool. After the addition of water, the mixture was filtered and the filtrate was acidified with concentrated hydrochloric acid. The precipitate was collected and recrystallized from dilute ethanol to give the title compound (42 g, 72%), m.p. 152°–153° C.

The following compounds were prepared in substantially the same manner as in Referential Example 2:

2-(4'-Acetylphenoxy)benzoic acid, m.p. 152°–153° C.

2-(4'-Ethoxycarbonylphenoxy)-5-methylbenzoic acid, m.p. 80°–90° C.

2-(4'-Acetylphenoxy)-5-methylbenzoic acid, m.p. 144°–145° C.

REFERENCE EXAMPLE 3

4-(2'-Carboxymethylphenoxy)phenylacetic acid:

(i) A solution of 2-(4'-ethoxycarbonylphenoxy)benzoic acid (35 g) in dry tetrahydrofuran (120 ml) was added dropwise to a stirred suspension of lithium aluminum hydride (9.3 g) in dry tetrahydrofuran (300 ml) at room temperature. After the addition, the mixture was refluxed with stirring for 4 hours, and then the excess of lithium aluminum hydride was destroyed by cautious addition of water. The mixture was concentrated and dilute hydrochloric acid was added to the residue. The resulting mixture was extracted with chloroform and the extracts were washed with water. Concentration of the dried extracts gave crude 4-(2'-hydroxymethylphenoxy)benzyl alcohol (25 g) as an oil, $IR\nu_{max}^{film}cm^{-1}$: 3300 (OH).

(ii) Thionyl chloride (51 g) was added dropwise to a solution of the above alcohol compound in chloroform (200 ml) at room temperature, and then the mixture was refluxed for 1 hour. The solvent was evaporated, a solution of the residue in toluene was washed with aqueous potassium carbonate and water, and dried over anhydrous sodium sulfate. Concentration of the solution gave crude 4-(2'-chloromethylphenoxy)benzyl chloride (27 g) as an oil, which showed no hydroxyl band in its IR spectrum.

(iii) A solution of the above chloride compound and sodium cyanide (13.5 g) in a mixture of dioxane (100 ml), ethanol (100 ml) and water (50 ml) was refluxed for 6 hours with stirring, followed by removal of the solvent in vacuo. A solution of the residue in toluene was washed with water, dried over anhydrous sodium sulfate and concentrated in vacuo to give crude 4-(2'-cyanomethylphenoxy)benzyl nitrile (23.3 g) as an oil. $IR\nu_{max}^{film}cm^{-1}$: 2240 (C≡N).

(iv) A solution of the above nitrile compound and potassium hydroxide (38 g) in a mixture of ethanol (300 ml) and water (75 ml) was refluxed for 16 hours with stirring. After evaporation of the ethanol in vacuo, the residue was acidified with hydrochloric acid and extracted with chloroform. The extracts were washed with water, dried over anhydrous sodium sulfate and concentrated. The oily residue was dissolved in toluene with warming and the solution cooled in an ice bath. The crystalline precipitate was collected and recrystallized from a mixture of ethanol and toluene to give the title compound (18.5 g), m.p. 150°–152° C.

the following compounds were prepared in substantially the same manner as in Referential Example 3:

dl-2-[4-(2'-Carboxymethylphenoxy)phenyl]propionic acid, m.p. 170°–172° C.

4-(2'-Carboxymethyl-4'-methylphenoxy)phenylacetic acid, m.p. 159°–160° C.

dl-2-[4-(2'-Carboxymethyl-4'-methylphenoxy)-phenyl]propionic acid, m.p. 129°–132° C.

REFERENCE EXAMPLE 4 dl-2-(10,11-Dihydro-11-oxodibenz[b,f]oxepin-2-yl)propionic acid:

Repeating the procedure of Example 1 using dl-2-[4-(2'-carboxymethylphenoxy)phenyl]propionic acid in place of dl-2-[4-(2'-carboxymethyl-4'-methylphenoxy)- phenyl]propionic acid gave the title compound, m.p. 152°–154° C.

EXAMPLE 11

|  | per 1,000 tablets |
|---|---|
| dl-2-(8-Methyl-10,11-dihydro-11-oxodibenz[b,f]oxepin-2-yl)-propionic acid (compound A) | 25 g |
| Corn starch | 28 g |
| Lactose | 60 g |
| Microcrystalline cellulose | 30 g |
| Hydroxypropylcellulose | 5 g |
| Light anhydrous silicic acid | 1 g |
| Magnesium stearate | 1 g |

The above components were blended, granulated and made into tablets by a conventional method to form 1,000 tablets each weighing 150 mg.

EXAMPLE 12

|  | per 1,000 capsules |
|---|---|
| 2-(2-Hydroxyethoxy)ethyl dl-2-(8-methyl-10,11-dihydro-11-oxodibenz[b,f]oxepin-2-yl)-propionate (compound E) | 25 g |
| Corn starch | 60 g |
| Lactose | 30 g |
| Microcrystalline cellulose | 84 g |
| Talc | 0.5 g |
| Magnesium stearate | 0.5 g |

The above components were blended, granulated and filled into 1,000 capsules by a conventional method.

EXAMPLE 13

|  | per 1,000 capsules |
|---|---|
| dl-2-(8-Methyl-10,11-dihydro-11-oxodibenzo[b,f]thiepin-2-yl)-propionic acid (compound C) | 25 g |
| Corn starch | 57 g |
| Lactose | 90 g |
| Hydroxypropylcellulose | 6 g |
| Talc | 1 g |
| Magnesium stearate | 1 g |

The above components were blended, granulated and filled into 1,000 capsules by a conventional method.

EXAMPLE 14

|  | per 1,000 suppositories |
|---|---|
| dl-2-(8-Methyl-10,11-dihydro-11-oxodibenz[b,f]oxepin-2-yl)-propionic acid (compound A) | 50 g |
| Anhydrous lanolin | 80 g |
| Witepsol W35 (glycerides of saturated fatty acids, a product of Dynamit Nobel Chemicals) | 1,370 g |

The above components were made into 1,000 suppositories each weighing 1,500 mg by a conventional method.

EXAMPLE 15

2-(2-Hydroxyethoxy)ethyl dl-2-

-continued

| | |
|---|---|
| (10,11-dihydro-11-oxodibenz[b,f]-oxepin-2-yl)propionate (compound D) | 10 g |
| Oleyl alcohol | 10 g |
| Propylene glycol | 150 g |
| Triethanolamine | 10 g |
| Isopropyl alcohol | 500 g |
| Carbopol 940 (carboxyvinyl polymer, a product of BF Goodrich Chemical Division) | 10 g |
| Purified water | 310 g |

The above components were made into 1% gels by a conventional method.

What we claim is:

1. A compound of the formula

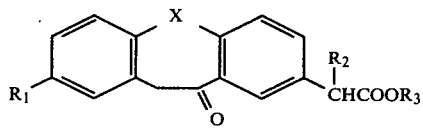

wherein X is oxygen or sulfur, each of $R_1$ and $R_2$ is hydrogen or methyl, and $R_3$ is hydrogen or 2-(2-hydroxyethoxy)ethyl, provided that when $R_1$ is hydrogen, $R_2$ is methyl and $R_3$ is 2-(2-hydroxyethoxy)ethyl, and when X is sulfur, both $R_1$ and $R_2$ are methyl, or a pharmaceutically acceptable salt thereof when $R_3$ is hydrogen.

2. A compound of the formula

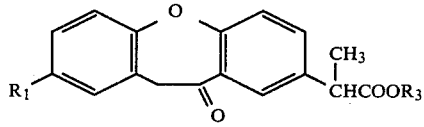

wherein $R_1$ is hydrogen or methyl, and $R_3$ is hydrogen or 2-(2-hydroxyethoxy)ethyl, provided that when $R_1$ is hydrogen, $R_3$ is 2-(2-hydroxyethoxy)ethyl, or a pharmaceutically acceptable salt thereof when $R_3$ is hydrogen.

3. A compound of the formula

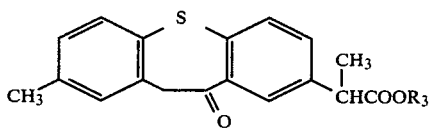

wherein $R_3$ is hydrogen or 2-(2-hydroxyethoxy)ethyl, or a pharmaceutically acceptable salt thereof when $R_3$ is hydrogen.

4. dl-2-(8-Methyl-10,11-dihydro-11-oxodibenz[b,f]oxepin-2-yl)propionic acid or a pharmaceutically acceptable salt thereof.

5. 8-Methyl-10,11-dihydro-11-oxodibenz[b,f]oxepin-2-acetic acid or a pharmaceutically acceptable salt thereof.

6. dl-2-(8-Methyl-10,11-dihydro-11-oxodibenzo[b,f]thiepin-2-yl)-propionic acid or a pharmaceutically acceptable salt thereof.

7. 2-(2-Hydroxyethoxy)ethyl dl-2-(10,11-dihydro-11-oxodibenz[b,f]oxepin-2-yl)propionate.

8. 2-(2-Hydroxyethoxy)ethyl dl-2-(8-methyl-10,11-dihydro-11-oxodibenz[b,f]oxepin-2-yl)propionate.

9. 2-(2-Hydroxyethoxy)ethyl 8-methyl-10,11-dihydro-11-oxodibenz[b,f]oxepin-2-acetate.

10. 2-(2-Hydroxyethoxy)ethyl dl-2-(8-methyl-10,11-dihydro-11-oxodibenzo[b,f]thiepin-2-yl)propionate.

* * * * *